United States Patent [19]

Suzuki et al.

[11] Patent Number: 5,705,671

[45] Date of Patent: Jan. 6, 1998

US005705671A

[54] METHOD FOR PRODUCING α-HYDROXY-β-AMINOCARBOXYLIC ACIDS

[75] Inventors: Takayuki Suzuki; Yutaka Honda; Kunisuke Izawa, all of Kawasaki, Japan

[73] Assignee: Ajinomoto Co., Inc., Tokyo, Japan

[21] Appl. No.: 725,714

[22] Filed: Oct. 4, 1996

[30] Foreign Application Priority Data

Oct. 4, 1995 [JP] Japan .................................. 7-257497

[51] Int. Cl.$^6$ .................................................. C07C 327/22
[52] U.S. Cl. ............................................ 558/253; 558/254
[58] Field of Search .................................. 558/253, 254

[56] References Cited

U.S. PATENT DOCUMENTS 4,599,198  7/1986  Hoover.

FOREIGN PATENT DOCUMENTS 0 543 343 A2  5/1993  European Pat. Off..
0 657 415 A1  6/1995  European Pat. Off..

OTHER PUBLICATIONS

Database CAPLUS on STN, Chemical Abstracts Service (Columbus, Ohio), Accession No. 1976:58996, Tsuchihashi, G. et al., JP 50-117717, abstract, 1976.

Database CAPLUS on STN, Chemical Abstracts Service (Columbus, Ohio), Accession No. 1975:125014, Tsuchihashi, G. et al. J. Am. Chem. Soc. 1975, 97(3), 596–9, abstract.

Pusino, A. et al. Gazzetta Chimica Italiana, 1984, 114, 395–8.

Andre Rosowsky et al., "Pteridines. I. β–Keto Sulfoxides and α–Keto Aldehyde Hemithioacetals as Pteridine Precursors. A New Selective Synthesis of 6–and 7–Substituted Pteridines", J. Org. Chem., vol. 38, No. 11, pp. 2073–2077, Jun. 1, 1973.

Theresa M. Williams et al., "dl–Isoserine and Related Compounds", J. Org. Chem., vol. 50, No.1, pp. 91–97, Jan. 11, 1985.

Yuji Oikawa et al., "A New Synthetic Method for Condensed Heterocycles, Carbozoles, Indoles, and Benzothiophenes, Based on Acid–Catalyzed Cyclization of β–Keto Sulfoxides", J. Org. Chem., vol. 41, No. 7, Apr. 2, 1976.

Tadashi Okuyama et al., "Reactions of Thiols With Phenylglyoxal to Give Thiomandelic S–Esters. Formation of Hemithioacetals and Thier Rearrangement", Bull. Chem. Soc. Jpn., vol. 55, No. 5, pp. 1493–1497, May 1982.

Chisato Mukai et al., "Highly Stereocontrolled Asymmetric Syntheses of Taxol and Taxotere C–13 Side Chain Analogues", Tetrahedron, vol. 49, No. 37, pp. 8323–8336, Sep. 10, 1993.

K. Matsuura et al., "Synthetic Studies of Carbohydrate Derivatives with the Photochemical Reaction I. Photochemical Addition of Thioacetic Acid, Benzyl Mercaptan and 1, 3–Dioxolane", Tetrahedron Letters, No. 33, pp. 2869–2872, 1970.

*Primary Examiner*—Michael G. Ambrose
*Attorney, Agent, or Firm*—Oblon, Spivak, McClelland, Maier & Neustadt, P.C.

[57] ABSTRACT

The present invention provides a simple and inexpensive method for producing α-hydroxy-β-aminocarboxylic acids and their esters. An ester of an N-protected α-amino acid ester is converted into a β-ketosulfoxide, which is then processed with an acid to give an α-ketohemimercaptal. Next, this is acylated and then processed with a base to obtain an N-protected α-acyloxy-β-amino-thioester, which is then saponified to obtain an intended compound. According to the method of the present invention, it is possible to produce α-hydroxy-β-aminocarboxylic acid derivatives, which are intermediates in producing various HIV protease inhibitors, renin inhibitors and carcinostatics, from a-amino acids. The method comprises reduced reaction steps, the selectivity in the method to give the intended product is high, and the yield of the product obtained is high.

4 Claims, No Drawings

5,705,671

METHOD FOR PRODUCING α-HYDROXY-β-AMINOCARBOXYLIC ACIDS

BACKGROUND OF THE INVENTION

1. Field of the Invention

The present invention relates to α-hydroxy-β-aminocarboxylic acid derivatives which are important as the ingredients constituting inhibitors for enzymes, such as HIV protease and renin, or constituting some carcinostatics. In particular, the compounds of the present invention are important constituents of the HIV protease inhibitor KNI-272 (see Chem. Pharm. Bull., 40, 2251 (1992)), the renin inhibitor KRI-1314 (see J. Med. Chem., 33, 2707 (1990)), the carcinostatic Bestatin (see Biochem. Pharmacol., 32, 1051 (1983)), and the carcinostatic Taxol (see Bull. Cancer, 80, 326 (1993)); comprising, as the constitutive ingredients, (2S,3S)-3-amino-2-hydroxy-4-phenylbutyric acid, (2R,3S)-3-amino-2-hydroxy-4-cyclohexylbutyric acid, (2S,3R)-3-amino-2-hydroxy-4-phenylbutyric acid, and (2R,3S)-phenylisoserine.

2. Discussion of the Background

Conventional methods for producing the above-mentioned compounds are known and rely on, the corresponding α-amino acids as starting materials. The methods comprise preparing N-protected α-aminoaldehydes from the starting acids, reacting them with prussic acid derivatives to give cyanohydrin intermediates and hydrolyzing them at the cyano group to obtain the intended compounds (see U.S. Pat. No. 4,599,198; Iizuka et al., J. Med. Chem., 33, 2707 (1990); M. T. Reets et al., Tetrahedron Lett., 29, 3295 (1988)). However, since these methods are defective because they require an oxidation-reduction step, they use toxic cyano derivatives and they produce, as intermediates, N-protected α-aminoaldehydes which are unstable in quantity production. Accordingly, they are not suitable for the production of large quantities of the compounds.

Another method is also known which comprises reacting a N-protected α-aminoaldehyde with nitromethane through an aldol reaction in the presence of an asymmetric catalyst, followed by hydrolyzing the resulting compound with an acid to obtain the intended product (see EP-657415). However, this method is also unsuitable for large-scale production of the product, since the intermediate α-aminoaldehyde is unstable and the asymmetric catalyst to be used is expensive.

Still another method is known which comprises reacting an N-protected α-aminocarboxylic acid chloride to be derived from the corresponding α-amino acid with trimethylsilyl cyanide to give an α-oxonitrile, then converting it into an α-ketocarboxylate and thereafter reducing it to obtain the intended product (see EP-543343). However, this method is also unsuitable to large-scale production of the product, since it uses such an expensive and toxic cyano compound.

SUMMARY OF THE INVENTION

Accordingly, one object of the present invention is to provide an industrial method for producing α-hydroxy-β-aminocarboxylic acids and their esters.

The present inventors have now found a method for stereoselectively producing α-hydroxy-β-aminocarboxylic acids and their esters, which comprises reacting a β-ketosulfoxide that is easily obtained from an N-protected aminocarboxylate, with an acid to give an α-keto-hemimercaptal, then acylating it to give an α-keto-hemimercaptal-carboxylate, and thereafter rearranging it in the presence of a base.

DETAILED DESCRIPTION OF THE EMBODIMENTS

Specifically, the present invention is a method for producing α-acyloxy-thioesters of the formula (II):

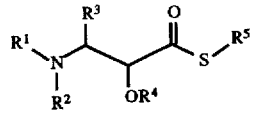

wherein $R^1$ represents hydrogen, an unsubstituted or substituted linear, branched or cyclic alkanoyl group having from 2 to 18 carbon atoms; an unsubstituted or substituted linear, branched or cyclic alkoxycarbonyl group having from 2 to 18 carbon atoms (such as t-butoxy carbonyl); an aralkyloxycarbonyl group having from 7 to 18 carbon atoms (such as benzyloxycarbonyl); or an unsubstituted or substituted benzyl group, or represents, together with $R^1$, a residue of a dibasic acid having from 8 to 18 carbon atoms;

$R^2$ represents a hydrogen atom or an optionally-substituted benzyl group, or represents, together with $R^{1'}$, a residue of a dibasic acid having from 8 to 18 carbon atoms;

$R^3$ represents an unsubstituted or substituted, linear, branched or cyclic alkyl group having from 1 to 18 carbon atoms (such as cyclohexylmethyl or isobutyl), an aralkyl group having from 7 to 18 carbon atoms (such as phenyl); or an aryl group having from 6 to 18 carbon atoms (such as benzyl);

$R^4$ represents an unsubstituted or substituted, linear, branched or cyclic alkanoyl group having from 2 to 18 carbon atoms (such as acetyl), or an arylcarbonyl group having from 7 to 18 carbon atoms (such as benzoyl); and $R^5$ represents an alkyl group having 1 or 2 carbon atoms (such as methyl), an aryl group having from 6 to 18 carbon atoms, or an aralkyl group having from 7 to 18 carbon atoms, which comprises rearranging, in the presence of a base, an α-keto-hemimercaptal-carboxylate of a general formula (I):

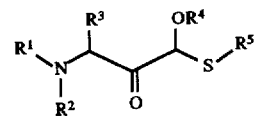

wherein $R^1$, $R^2$, $R^3$, $R^4$ and $R^5$ have the same meanings as above.

Compounds of the formula (I) can be obtained by (i) reacting an N-protected α-aminocarboxylate of the formula (III):

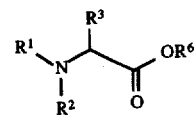

wherein $R^1$, $R^2$ and $R^3$ have the same meanings as above; and $R^6$ represents a linear or branched alkyl group having from 1 to 5 carbon atoms, an aryl group having from 6 to 18 carbon atoms, or an aralkyl group having from 7 to 18 carbon atoms, with a carbanion of a general formula (IV):

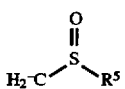

wherein R⁵ has the same meaning as above, to obtain β-ketosulfoxide of the formula (V):

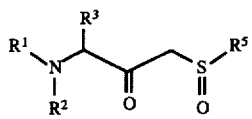

wherein R¹, R², R³ and R⁵ have the same meanings as above, (ii) then reacting the sulfoxide with an acid to obtain an α-ketohemimercaptal of a general formula (VI):

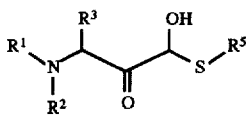

wherein R¹, R², R³ and R⁵ have the same meanings as above, and thereafter (iii) acylating the hemimercaptal.

N-protected α-aminocarboxylates (III) which are used in the present invention can be derived from α-aminocarboxylic acids according to conventional means used in ordinary peptide synthesis. The α-aminocarboxylic acids may be naturally-existing amino acids or synthetic amino acids. Their esters are represented by the following structural formula:

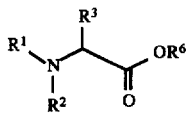

wherein R³ represents an unsubstituted or substituted, linear, branched or cyclic alkyl group having from 1 to 18 carbon atoms, an aralkyl group having from 7 to 18 carbon atoms, or an aryl group having from 6 to 18 carbon atoms. Suitable examples include benzyl, cyclohexyl-methyl, phenyl, isopropyl, isobutyl and sec-butyl groups. Suitable amino acid moieties include, for example, phenylalanine, cyclohexylalanine, phenylglycine, valine, leucine and iso-leucine.

R¹ and R² in the N-protected α-aminocarboxylates (III) are amino-protecting groups or are the protected condition of the esters. The protecting groups are not specifically defined but may be any ones that are used in ordinary peptide synthesis. For example, R¹ may be an unsubstituted or substituted, linear, branched or cyclic alkanoyl group having from 2 to 18 carbon atoms, an unsubstituted or substituted, linear, branched or cyclic alkoxycarbonyl group having from 2 to 18 carbon atoms, an aralkyloxycarbonyl group having from 7 to 18 carbon atoms, or an unsubstituted or substituted benzyl group, or may be, together with R², a residue of a dibasic acid having from 8 to 18 carbon atoms. R² may be a hydrogen atom or an unsubstituted or substituted benzyl group, or may be, together with R², a residue of a dibasic acid having from 8 to 18 carbon atoms. Namely, R¹ and R² each are independently a hydrogen atom or an amino-protecting group, or they form, as combined, a bifunctional, amino-protecting group. The amino-protecting group includes, for example, so-called, urethane-type protecting groups such as a benzyloxycarbonyl group and a t-butyloxycarbonyl group; acyl-type protecting groups such as an acetyl group and a benzoyl group; and a benzyl-type protecting groups such as a benzyl group and a dibenzyl group. One example of the bifunctional amino-protecting group is a phthaloyl group.

R⁶ in the N-protected α-aminocarboxylates (III) indicates an ester residue of an amino acid. R⁶ may be a linear or branched alkyl group having from 1 to 5 carbon atoms (such as methyl or ethyl), an aryl group having from 6 to 18 carbon atoms (such as benzyl), or an aralkyl group having from 7 to 18 carbon atoms. Suitable examples include methyl, ethyl, propyl, isopropyl, butyl, isobutyl, sec-butyl, t-butyl and benzyl groups.

The reaction of the N-protected α-aminocarboxylate (III) with the carbanion (IV) to give the β-ketosulfoxide (V) may be conducted by dissolving the N-protected α-aminocarboxylate in an inert solvent such as tetrahydrofuran, diethyl ether or methyl t-butyl ether, followed by dropwise adding the resulting solution to a solution of a carbanion of methylsulfoxide as prepared in the manner as mentioned below. The temperature at which the former solution is dropwise added to the latter solution may fall between −70° C. and 20° C., preferably between −20° C. and 10° C. The reaction temperature may fall between −70° C. and 20° C., preferably between −20° C. and 10° C. Typically, 2.0 to 5.0 equivalents of the carbanion (IV) and 2.0 to 5.0 equivalents of base are used per equivalent of N-protected α-amino-carboxylate (III).[1]

[1] When the amino group has a hydrogen atom(s), at least 3 equivalents of the reagent is required. When the amino group does not have a hydrogen atom, at least 2 equivalents of the reagent is required.

The carbanion can be prepared by reacting a methylsulfoxide of the formula (III') with a base.

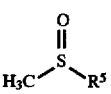

R⁵ in the methylsulfoxide of formula (III') represents an alkyl group having 1 or 2 carbon atoms, an aryl group having from 6 to 18 carbon atoms, or an aralkyl group having from 7 to 18 carbon atoms. Specific examples of the methylsulfoxide include dimethylsulfoxide, methylethylsulfoxide, methylphenylsulfoxide, and methyl-p-tolylsulfoxide. Of these, preferred is dimethylsulfoxide in view of the economical aspect and the easy availability.

To prepare the anion, any and every base capable of forming it can be employed. Preferred base include sodium amide, sodium hydride, potassium t-butoxide and lithium diisopropylamide. The anion is suitably prepared in an inert solvent such as dimethylsulfoxide, tetrahydrofuran, diethyl ether or methyl t-butyl ether or a mixture thereof.

The temperature at which the anion is prepared falls between −70° C. and 80° C., preferably between −20° C. and 70° C. The time to be taken for the preparation may be approximately from 30 minutes to 2 hours. The concentration of the anion thus prepared may be approximately from 0.5 mol/liter to 5 mol/liter.

To post-treat the reaction mixture, it is poured into an aqueous, acidic solution or, alternatively, the latter is poured into the former. The aqueous, acidic solution may be, for example, an aqueous solution of citric acid, acetic acid or hydrochloric acid.

The reaction gives a second asymmetric center on the sulfur atom in the product, which, therefore, generally consists of two diastereomers or two pairs of diastereomers depending on the starting compound, either a racemic amino acid derivative or an optically-active amino acid derivative. These diastereomers can be used in the next reaction without being specifically isolated. When used to produce the α-keto-hemimercaptal (VI) in the next reaction, the β-ketosulfoxide need not be purified but a crude product or a non-processed reaction mixture comprising it can be directly used in the next reaction. β-ketosulfoxides (V) as produced after the reaction are novel compounds.

To obtain α-keto-hemimercaptals (VI) by reacting the ketosulfoxide (V) as obtained in the above with an acid, for example, the β-ketosulfoxide is dissolved in a water-soluble solvent, such as dimethylsulfoxide, dimethylformamide, tetrahydrofuran, dioxane, or alcohol (e.g., methanol, ethanol), and then an aqueous solution of an acid, such as hydrochloric acid, sulfuric acid, hydrobromic acid or p-toluenesulfonic acid is added thereto and reacted at from −20° C. to 50° C. The reaction solvent is preferably dimethylsulfoxide, and the acid is preferably hydrochloric acid, since few side reactions occur. The reaction temperature is preferably from 0° C. to 30° C.

α-keto-hemimercaptals can also be obtained by reacting the β-ketosulfoxide with an acid anhydride followed by hydrolyzing the product. The solvent usable in the reaction includes, for example, dichloromethane, chloroform, tetrahydrofuran, dioxane, diethyl ether, dimethylformamide, dimethylacetamide, pyridine, toluene and ethyl acetate. The acid anhydride includes, for example, acetic anhydride, trifluoroacetic anhydride and trichloroacetic anhydride. In order to smoothly carry out the reaction, a base, such as pyridine, 2-picoline, 2,6-lutidine, 2,4,6-collidine or triethylamine, can be added to the reaction system.

In the next reaction of acylating the hydroxyl group of the α-keto-hemimercaptal (VI) to give the α-keto-hemimercaptalcarboxylate (I), the α-keto-hemimercaptal is dissolved in a solvent which is generally used in ordinary acylation, such as dichloromethane, chloroform, tetrahydrofuran, dioxane, diethyl ether, dimethylformamide, dimethylacetamide, pyridine, toluene or ethyl acetate, and then treated with an acylating agent. The acylating agent may be selected from acid chlorides, acid bromides and acid anhydrides. Suitable examples include acetyl chloride, acetic anhydride, benzoyl chloride and benzoyl bromide. In order to smoothly carry out the reaction, a base, such as pyridine, 2-picoline, 2, 6-lutidine, 2,4,6-collidine or triethylamine, can be added to the reaction system. The reaction temperature may be from −50° C. to 50° C. but is preferably from −20° C. to 30° C.

α-keto-hemimercaptal-carboxylates (I) can also be obtained by reacting the β-ketosulfoxide (V) with an acid anhydride. The solvent usable in the reaction includes, for example, dichloromethane, chloroform, tetrahydrofuran, dioxane, diethyl ether, dimethylformamide, dimethylacetamide, pyridine, toluene and ethyl acetate. The acid anhydride includes, for example, acetic anhydride and trichloroacetic anhydride. In order to smoothly carry out the reaction, a base, such as pyridine, 2-picoline, 2,6-lutidine, 2,4,6-collidine or triethylamine, can be added to the reaction system.

The α-keto-hemimercaptal-carboxylate prepared as above is rearranged in the presence of a base into a β-amino-α-acyloxythioester (II). The base includes, for example, 1,8-diazabicyclo[5.4.0]undec-7-ene, 1,5-diazabicyclo[4.3.0]non-5-ene, 4-dimethylaminopyridine, pyridine, 2-picoline, 2,6-lutidine, 2,4,6-collidine, triethylamine and diisopropylethylamine. Of these, preferred are 1,8-diazabicyclo[5.4.0]undec-7-ene and 1,5-diazabicyclo[4.3.0]non-5-ene. The solvent usable in the reaction includes, for example, dichloromethane, chloroform, tetrahydrofuran, dioxane, diethyl ether, dimethylformamide, dimethylacetamide, dimethylsulfoxide, pyridine, toluene, ethyl acetate, methanol, ethanol, isopropanol and t-butanol.

The reaction temperature may be from −80° C. to 50° C., but, in general, the diastereoselectivity in the reaction is higher at lower reaction temperatures.

The reaction also gives a second asymmetric center in the product, which generally consists of two diastereomers or two pairs of diastereomers depending on the starting compound, either a racemic amino acid derivative or an optically-active amino acid derivative. The ratio of the diastereomers formed or, that is, the diastereoselectivity varies, depending on the solvent used and the reaction temperature.

The diastereomers can be isolated, for example, through column chromatography or crystallization.

The compound as produced according to the method of the present invention has two asymmetric centers (if $R^1$ and $R^2$ do not have any additional asymmetric center) and therefore includes four stereoisomers. Only one of the two asymmetric centers is formed through the reaction in the method of the present invention, while the stereo-configuration with respect to the other asymmetric center is kept as such throughout the method. Therefore, when an optically-active α-amino derivative is used as the starting compound in the method of the present invention, it always gives a mixture of two diastereomers. Because these have different physical properties, these two diastereomers can be separated from each other. Accordingly, the present invention is especially advantageous in producing α-hydroxy-β-amino acids having the same stereo-configuration.

α-carboxy-thioesters (II) as obtained after the above-mentioned reaction can be hydrolyzed or alcoholyzed into N-protected β-amino-α-hydroxycarboxylic acids or their esters of the formula (VII):

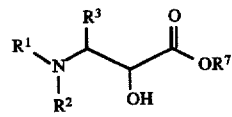

wherein $R^1$, $R^2$ and $R^3$ have the same meanings as above; and $R^7$ represents a hydrogen atom, an alkyl group having from 1 to 8 carbon atoms, an aryl group having from 6 to 18 carbon atoms, or an aralkyl group having from 7 to 18 carbon atoms.

The solvent usable in the hydrolysis includes, for example, alcoholic solvents such as methanol, ethanol and 2-propanol, and mixed solvents comprising tetrahydrofuran or dioxane, and water. The reagent to be used in the reaction is a metal hydroxide, preferably sodium hydroxide or potassium hydroxide. The reaction temperature may fall between −20° C. and 80° C., but preferably between 0° C. and 40° C. Typically, 1.0 to 2.0, preferably 1.2, equivalents of the solvent may be used.

The solvent usable in the alcoholysis may be an alcohol corresponding to the intended ester, preferably methanol or ethanol. The base to be used in the reaction includes, for example, metal alkoxides, preferably sodium methoxide and sodium ethoxide; metal hydroxides, preferably sodium hydroxide and potassium hydroxide; and metal carbonates, preferably sodium carbonate and potassium carbonate.

Having generally described this invention, a further understanding can be obtained by reference to certain specific examples which are provided herein for purposes of illustration only and are not intended to be limiting unless otherwise specified.

EXAMPLES

Example 1

Production of N,N-dibenzyl-(L)-phenylalanine benzyl ester:

25.0 g (151.3 mmol) of (L)-phenylalanine and 66.67 g (482.4 mmol) of potassium carbonate were dissolved in 100 ml of water, and then 57.51 g (454.3 mmol) of benzyl chloride was added thereto and stirred under heat at 95° C. for 19 hours. After having been cooled to room temperature, this was subjected to phase separation with 67 ml of n-heptane and 50 ml of water. The organic layer thus separated was washed two times with 50 ml of a solution of methanol/water (=1/2) and then dried with anhydrous sodium sulfate. This was filtered and concentrated to obtain 61.64 g (90.5 wt. %, 121.8 mmol) of the above-entitled compound. The yield was 84.7%.

$^1$H-NMR (300 MHz, CDCl$_3$)

δ: 3.00 (dd, 1H), 3.14 (dd, 1H), 3.53 (d, 2H), 3.71 (t, 1H), 3.92 (d, 2H), 5.12 (d, 1H), 5.23 (d, 1H), 6.99–7.40 (m, 20H).

Mass spectrum (FAB) 436 (MH$^+$)

Example 2

Production of (3S)-3-(N,N-dibenzyl)amino-1-methylsulfinyl-2-oxo-4-phenylbutane:

3.76 g (96.39 mmol) of sodium amide was suspended in 40 ml of dimethylsulfoxide and heated at from 74° to 75° C. for 30 minutes. 40 ml of tetrahydrofuran was added to the resulting solution and cooled to 0° C. To this was dropwise added a solution of 15.47 g (90.5 wt. %, 32.14 mmol) of N,N-dibenzyl-(L)-phenylalanine benzyl ester as dissolved in 20 ml of tetrahydrofuran, while keeping it at 0° C. After these were reacted at 0° C. for 30 minutes, 120 ml of an aqueous solution of 10% citric acid and 100 ml of ethyl acetate were added to the reaction mixture, which was thus subjected to phase separation. The aqueous layer thus separated was extracted once with 50 ml of ethyl acetate, and the resulting extract was combined with the previously-separated organic layer and then washed with 60 ml of a saturated saline solution. This was dried with anhydrous sodium sulfate, filtered and concentrated, and the resulting residue was purified through silica gel column chromatography (hexane/ethyl acetate=from 2/1 to 1/3) and then crystallized in toluene/hexane to obtain 11.16 g of the above-entitled compound. The yield was 85.6%. The integral ratio in $^1$H-NMR of the compound verified that the ratio of the diastereomers constituting it is about 1:1.

$^1$H-NMR (300 MHz, CDCl$_3$)

δ: 2.27 (s, 3/2H), 2.35 (s, 3/2H), 2.97 (dd, 1H), 3.14 (dd, 1/2H), 3.19 (dd, 1/2H), 3.55–3.65 (m, 7/2H), 3.75 (d, 1/2H), 3.85 (d, 2H), 4.01 (d, 1/2H), 4.07 (d, 1/2H), 7.10–7.40 (m, 15H).

Mass spectrum (FAB) 406 (MH$^+$)

Example 3

Production of (3S)-3-(N,N-dibenzyl)amino-1-hydroxy-1-methylthio-2-oxo-4-phenylbutane:

309.6 mg (0.763 mmol) of (3S)-3-(N,N-dibenzyl)amino-1-methylsulfinyl-2-oxo-4-phenylbutane was dissolved in 6 ml of dimethylsulfoxide, and 1.5 ml of 2N hydrochloric acid was added thereto and stirred at room temperature for 16 hours. While being cooled in an ice bath, this was neutralized with 5 ml of a saturated aqueous solution of sodium hydrogen carbonate, and then subjected to phase separation with 20 ml of ethyl acetate and 10 ml of water. The resulting aqueous layer was extracted twice with 10 ml of ethyl acetate. The organic layers were combined, then washed with 20 ml of water and 20 ml of a saturated saline solution in that order, and thereafter dried with anhydrous sodium sulfate. This was filtered and concentrated to obtain 371.5 mg of a crude product of the above-entitled compound.

$^1$H-NMR (300 MHz, CDCl$_3$)

δ: 1.13 (s, 3H), 3.05 (dd, 1H), 3.18 (dd, 1H), 3.52 (d, 2H), 3.82 (d, 2H), 4.24 (dd, 1H), 5.44 (d, 1H), 7.12–7.38 (m, 15H)

Example 4

Production of (3S)-1-acetoxy-3-(N,N-dibenzyl)amino-1-methylthio-2-oxo-4-phenylbutane:

173.0 mg of the crude product of (3S)-3-(N,N-dibenzyl)amino-1-hydroxy-1-methylthio-2-oxo-4-phenylbutane as obtained in Example 3 was dissolved in 4 ml of dichloromethane and 0.1 ml of pyridine, and 0.05 ml (0.703 mmol) of acetyl chloride was added thereto, while cooling in an ice bath, and stirred at room temperature for 30 minutes. The reaction mixture was extracted with 5 ml of 0.2N hydrochloric acid and 10 ml of dichloromethane as added thereto. The resulting organic layer was washed with 5 ml of a saturated aqueous solution of sodium hydrogen carbonate and 8 ml of a saturated saline solution, and then dried with anhydrous sodium sulfate. This was filtered and concentrated, and the resulting residue was purified through partitioning, silica gel thin-layer chromatography to obtain 144.8 mg (0.324 mmol) of the above-entitled compound. The yield was 91.1% (two steps). The integral ratio in $^1$H-NMR of the compound verified that the compound is a mixture of diastereomers of about 20:1. The data of the major diastereomer are shown below. $^1$H-NMR (300 MHz, CDCl$_3$)

δ: 1.18 (s, 3H), 2.14 (s, 3H), 3.03 (dd, 1H), 3.17 (1H, dd), 3.54 (d, 2H), 3.87 (d, 2H), 4.22 (dd, 1H), 6.41 (s, 1H), 7.10–7.40 (m, 15H).

Mass spectrum (FAB) 448 (MH$^+$)

Example 5

Production of methylthio (3S)-(2R,S)-2-acetoxy-3-(N,N-dibenzyl)amino-4-phenylbutyrate:

89.5 mg (0.200 mmol) of (3S)-1-acetoxy-3-(N,N-dibenzyl)amino-1-methylthio-2-oxo-4-phenylbutane was dissolved in 2 ml of toluene and cooled to −30° C., and 0.03 ml (0.201 mmol) of 1,8-diazabicyclo[5.4.0]undec-7-ene was added thereto. After having been stirred at −30° C. for 23 hours, this was extracted with 7 ml of toluene and 6 ml of 0.2N hydrochloric. The resulting organic layer was washed with 5 ml of a saturated aqueous solution of sodium hydrogen carbonate and 5 ml of a saturated saline solution, then dried with anhydrous sodium sulfate, filtered and concentrated. The resulting residue was purified through partitioning, silica gel thin-layer chromatography to obtain 95.6 mg (0.214 mmol) of the above-entitled compound. The yield was 106.8%. The integral ratio in $^1$H-NMR of the compound verified that the ratio of the diastereomers constituting it, of (2S,3S):(2R,3S) is about 58:42.

(2S,3S) diastereomer:

$^1$H-NMR (300 MHz, CDCl$_3$)

δ: 2.23 (s, 3H), 2.24 (s, 3H), 2.80 (dd, 1H), 3.08 (dd, 1H), 3.39 (d, 2H), 3.65 (ddd, 1H), 3.88 (d, 2H), 5.83 (d, 1H), 6.96–7.30 (m, 15H).

Mass spectrum (FAB) 448 (MH$^+$)

(2R,3S) diastereomer:
¹H-NMR (300 MHz, CDCl₃)

δ: 2.23 (s, 3H), 2.24 (s, 3H), 2.81 (dd, 1H), 3.10 (dd, 1H), 3.56 (d, 2H), 3.59 (m, 1H), 4.04 (d, 2H), 5.07 (d, 1H), 6.96–7.30 (m, 15H).

Mass spectrum (FAB) 448 (MH⁺)

Example 6

Production of methylthio (3S)-(2R,S)-2-acetoxy-3-(N,N-dibenzyl)amino-4-phenylbutyrate:

50.6 mg (0.113 mmol) of (3S)-1-acetoxy-3-(N,N-dibenzyl)amino-1-methylthio-2-oxo-4-phenylbutane was dissolved in 1.1 ml of dimethylformamide and cooled to −30° C., and 0.02 ml (0.134 mmol) of 1,8-diazabicyclo[5.4.0]undec-7-ene was added thereto. After having been stirred at −30° C. for 1 hour and 15 minutes, this was extracted with 10 ml of ethyl acetate and 6 ml of 0.2N hydrochloric acid. The resulting organic layer was washed with 6 ml of water and 8 ml of a saturated saline solution, then dried with anhydrous sodium sulfate, filtered and concentrated. The resulting residue was purified through partitioning, silica gel thin-layer chromatography to obtain 44.6 mg (0.100 mmol) of the above-entitled compound. The yield was 88.2%. The integral ratio in ¹H-NMR of the compound verified that the ratio of the diastereomers constituting it, of (2S,3S):(2R,3S), is about 92:8.

Example 7

Production of (3S)-1-benzoxy-3-(N,N-dibenzyl)amino-1-methylthio-2-oxo-4-phenylbutane:

671.2 mg (1.655 mmol) of (3S)-3-(N,N-dibenzyl)amino-1-methylsulfinyl-2-oxo-4-phenylbutane was dissolved in 10 ml of dimethylsulfoxide and 7 ml of tetrahydrofuran, and 5 ml of 2N hydrochloric acid was added thereto and stirred at room temperature for 15 hours. While being cooled in an ice bath, this was neutralized with 15 ml of a saturated aqueous solution of sodium hydrogen carbonate, and then subjected to phase separation with 50 ml of ethyl acetate and 50 ml of water as added thereto. The resulting aqueous layer was extracted twice with 25 ml of ethyl acetate. The organic layers were combined, washed with 50 ml of water and 50 ml of a saturated saline solution in that order, and then dried with anhydrous sodium sulfate. This was filtered and concentrated to obtain 371.5 mg of a crude product.

The crude product was dissolved in 17 ml of dichloromethane and 0.67 ml of pyridine, and 0.23 ml (1.95 mmol) of benzoyl bromide was added thereto, while cooling it in an ice bath, and then stirred at room temperature for 35 minutes. The reaction mixture was extracted with 20 ml of 5N hydrochloric acid and 20 ml of dichloromethane as added thereto. The resulting organic layer was washed with 15 ml of a saturated aqueous solution of sodium hydrogen carbonate and 20 ml of a saturated saline solution, and the dried with anhydrous sodium sulfate. This was filtered and concentrated, and the resulting residue was purified through silica gel column chromatography (hexane/ethyl acetate= from 15/1 to 10/1) to obtain 774.3 mg (1.519 mmol) of the above-entitled compound. The yield was 91.8% (two steps). The integral ratio in ¹H-NMR of the compound verified that the compound is a mixture of diastereomers of about 13:1. The data of the major diastereomer are shown below.

¹H-NMR (300 MHz, CDCl₃)

δ: 1.31 (s, 3H), 3.05 (dd, 1H), 3.20 (dd, 1H), 3.57 (d, 2H), 3.91 (d, 2H), 4.27 (dd, 1H), 6.66 (s, 1H), 7.12–7.60 (m, 18H), 8.06–8.10 (m, 2H).

Mass spectrum (FAB) 510 (MH⁺)

Example 8

Production of methylthio (3S)-(2R,S)-2-benzoxy-3-N,N-dibenzyl)amino-4-phenylbutyrate:

54.2 mg (0.106 mmol) of (3S)-1-benzoxy-3-N,N-dibenzylamino-1-methylthio-2-oxo-4-phenylbutane was dissolved in 1.1 ml of toluene and cooled to 0° C., and 0.03 ml (0.201 mmol) of 1,8-diazabicyclo[5.4.0]undec-7-ene was added thereto. After having been stirred at 0° C. for 2 hours and 20 minutes, this was extracted with 10 ml of toluene and 6 ml of 0.2N hydrochloric acid as added thereto. The resulting organic layer was washed with 5 ml of water, 5 ml of a saturated aqueous solution of sodium hydrogen carbonate and 5 ml of a saturated saline solution, then dried with anhydrous sodium sulfate, filtered and concentrated. The resulting residue was purified through partitioning, silica gel thin-layer chromatography to obtain 45.0 mg (0.088 mmols) of the above-entitled compound. The yield was 83.3%. The integral ratio in ¹H-NMR of the compound verified that the ratio of the diastereomers constituting it, of (2S,3S):(2R,3S), is about 50:50.

(2S, 3S) diastereomer:
¹H-NMR (300 MHz, CDCl₃)

δ: 2.23 (s, 3H), 2.97 (dd, 1H), 3.22 (dd, 1H), 3.43 (d, 2H), 3.78 (m, 1H), 3.93 (d, 2H), 6.11 (d, 1H), 7.01–7.26 (m, 15H), 7.50–7.56 (m, 2H), 7.63–7.68 (m, 1H), 8.17–8.19 (m, 2H).

Mass spectrum (FAB) 510 (MH⁺)

(2R, 3S) diastereomer:
¹H-NMR (300 MHz, CDCl₃)

δ: 2.24 (s, 3H), 2.90 (dd, 1H), 3.15 (dd, 1H), 3.65 (d, 2H), 3.74 (m, 1H), 4.15 (d, 2H), 5.37 (d, 1H), 7.02–7.05 (m, 2H), 7.19–7.37 (m, 13H), 7.43–7.48 (m, 2H), 7.58.8.63 (m, 1H), 8.09–8.12 (m, 2H).

Mass spectrum (FAB) 510 (MH⁺)

The mixture of diastereomers as obtained in Example 8 was crystallized in ethyl acetate/hexane to give only crystals of the (2R,3S) diastereomer.

Example 9

Production of methylthio (3S)-(2R,S)-2-benzoxy-3-(N,N-dibenzyl)amino-4-phenylbutyrate:

54.2 mg (0.106 mmol) of (3S)-1-benzoxy-3-(N,N-dibenzyl)amino-1-methylthio-2-oxo-4-phenylbutane was dissolved in 1.1 ml of dimethylformamide and cooled to −30° C., and 0.02 ml (0.134 mmol) of 1,8-diazabicyclo[5.4.0]undec-7-ene was added thereto. After having been stirred at −30° C. for 30 minutes, this was extracted with 15 ml of ethyl acetate and 10 ml of 0.2N hydrochloric acid as added thereto. The resulting organic layer was washed with 10 ml of water and 8 ml of a saturated saline solution, then dried with anhydrous sodium sulfate, filtered and concentrated. The resulting residue was purified through partitioning, silica gel thin-layer chromatography to obtain 50.1 mg (0.098 mols) of the above-entitled compound. The yield was 83.3%. The integral ratio in ¹H-NMR of the compound verified that the ratio of the diastereomers constituting it, of (2S,3S):(2R,3S), is about 87:13.

Example 10

Production of (3S)-(2R,S)-3-(N,N-dibenzyl)amino-2-hydroxy-4-phenylbutyric acid:

87.1 mg (0.171 mmol) of methylthio (3S)-(2R,S)-2-benzoxy-3-N,N-dibenzylamino-4-phenylbutyrate was dissolved in 1.7 ml of tetrahydrofuran, and 0.68 ml of an aqueous solution of 1N sodium hydroxide was added thereto and stirred at room temperature for 2 days. After having been concentrated, this was subjected to phase separation with 2 ml of water, 7 ml of dichloromethane and 0.68 ml of 1N hydrochloric acid was added thereto. The resulting aqueous layer was extracted twice with 4 ml of dichloromethane. The organic layers were combined and dried with anhydrous sodium sulfate, then filtered and concentrated, and the resulting residue was purified through partitioning, silica gel thin-layer chromatography to obtain 44.9 mg of the above-entitled compound. The yield was 69.9

Mass spectrum (FAB) 376 (MH$^+$)

Example 11

Production of methyl (3S)-(2R,S)-3-N,N-dibenzylamino-2-hydroxy-4-phenylbutyrate:

53.6 mg (0.105 mmol) of methylthio (3S)-(2R, S)-2-benzoxy-3-N,N-dibenzylamino-4-phenylbutyrate was dissolved in 2 ml of methanol and 0.5 ml of tetrahydrofuran, and 0.04 ml of sodium methoxide (28% methanolic solution) was added thereto and stirred at room temperature for 3 hours and 20 minutes. After having been concentrated, this was subjected to phase separation with 20 ml of ethyl acetate, 5 ml of water and 0.5 ml of 1N hydrochloric acid as added thereto. The resulting organic layer was washed with a saturated saline solution. This was dried with anhydrous sodium sulfate, then filtered and concentrated, and the resulting residue was purified through partitioning, silica gel thin-layer chromatography to obtain 9.8 mg (0.0252 mmol; yield 24.0%) of (2S,3S) diastereomer of the above-entitled compound and 4.5 mg (0.0116 mmol; yield 11.0%) of (2R,3S) diastereomer thereof.

$^1$H-NMR (300 MHz, CDCl$_3$)

δ: 2.81 (dd, 1H), 3.03 (dd, 1H), 3.10 (br. d, 1H, —OH), 3.42 (dt, 1H), 3.53 (s, 3H), 3.66 (d, 2H), 3.8 1 (d, 2H), 4.48 (m, 1H), 7.05–7.29 (m, 15H).

Mass spectrum (FAB) 390 (MH$^+$)

(2R, 3S) diastereomer:

$^1$H-NMR (300 MHz, CDCl$_3$)

δ: 3.05–3.24 (m, 4H), 3.41 (s, 3H), 3.46 (d, 2H), 4.00 (br. t, 1H), 4.12 (d, 2H), 7.19–7.35 (m, 15H).

Mass spectrum (FAB) 390 (MH$^+$)

Example 12

Production of N-benzyloxycarbonyl-(L)-phenylalanine methyl ester:

20.0 g (92.73 mmol) of (L)-phenylalanine methyl ester hydrochloride was suspended in 93 ml of toluene, and 15.82 g (92.73 mmols) of benzyl chloroformate was added thereto. 130 ml of an aqueous solution of 1M sodium carbonate was dropwise added thereto, while keeping it at 7° C. or lower, and stirred for 3 hours. After this was subjected to phase separation, the resulting organic layer was washed with 60 ml of 0.1N hydrochloric acid and 60 ml of a saturated aqueous solution of sodium hydrogen carbonate, and then dried with anhydrous sodium sulfate. This was filtered and concentrated to obtain 28.75 g (96.8 wt. %, 88.81 mmol) of the above-entitled compound. The yield was 95.8%.

$^1$H-NMR (300 MHz, CDCl$_3$)

δ: 3.11 (m, 2H), 3.72 (s, 3H), 4.66 (m, 1H), 5.09 (s, 2H), 5.21 (br. d, 1H, —NH), 7.08–7.39 (m, 10H).

Mass spectrum (FAB) 314 (MH$^+$)

Example 13

Production of (3S)-3-(N-benzyloxycarbonyl)amino-1-methylsulfinyl-2-oxo-4-phenylbutane:

4.98 g (127.7 mmol) of sodium amide was suspended in 40 ml of dimethylsulfoxide and heated at from 72° to 76° C. for 50 minutes. 50 ml of tetrahydrofuran was added thereto and cooled to 0° C. To this was dropwise added a solution of 10.33 g (96.8 wt. %, 31.91 mmol) of N-benzyloxycarbonyl-(L)-phenylalanine methyl ester as dissolved in 20 ml of tetrahydrofuran, while keeping it at 0° C. After these were reacted at 0° C. for 1 hour, the reaction mixture was extracted with 120 ml of an aqueous solution of 10% citric acid and 100 ml of dichloromethane as added thereto. The resulting aqueous layer was extracted once with 60 ml of dichloromethane. The resulting organic layers were combined and washed with 80 ml of a saturated saline solution. This was dried with anhydrous sodium sulfate, then filtered and concentrated, and the resulting residue was crystallized in dichloromethane/hexane to obtain 8.14 g (22.65 mmols) of the above-entitled compound. The yield was 71.0%. The integral ratio in $^1$H-NMR of the compound verified that the compound is a mixture of diastereomers of about 3:1.

$^1$H-NMR (300 MHz, CDCl$_3$)

δ: 2.63 (s, 3/4H), 2.66 (s, 9/4H), 2.94–3.01 (m, 1H), 3.12–3.21 (m, 1H), 3.57 (d, 3/4H), 3.69 (d, 1/4H), 3.89 (d, 1/4H), 4.04 (d, 3/4H), 4.45–4.59 (m, 1H), 5.07 (m, 2H), 5.44 (br. d, 1/4H), 5.64 (br. s, 3/4H), 7.14–7.39 (m, 10H).

Mass spectrum (FAB) 360 (MH+)

Example 14

Production of (3S)-3-(N-benzyloxycarbonyl)amino-1-hydroxy-1-methylthio-2-oxo-4-phenylbutane:

708.6 mg (1.971 mmol) of (3S)-3-N-benzyloxycarbonylamino-1-methylsulfinyl-2-oxo-4-phenylbutane was dissolved in 15 ml of dimethylsulfoxide and 6 ml of tetrahydrofuran, and 7.5 ml of 2N hydrochloric acid was added thereto and stirred at room temperature for 18 hours. While being cooled in an ice bath, this was neutralized with 15 ml of a saturated aqueous solution of sodium hydrogen carbonate, and then subjected to phase separation with 50 ml of ethyl acetate and 50 ml of water. The resulting aqueous layer was extracted twice with 25 ml of ethyl acetate. The organic layers were combined, washed with 50 ml of water and 30 ml of a saturated saline solution in that order, and then dried with anhydrous sodium sulfate. This was filtered and concentrated, and the resulting residue was crystallized in hexane/ethyl acetate to obtain 659.7 mg (1.83S mmol) of a crude product of the above-entitled compound. The yield was 93.2%.

$^1$H-NMR (300 MHz, CDCl$_3$)

δ: 1.78 (s, 3H), 2.97 (dd, 1H), 3.24 (dd, 1H), 3.87 (dd, 1H), 4.86 (m, 1H), 5.05 (m, 2H), 5.55 (d, 1H), 7.18–7.39 (m, 10H).

Mass spectrum (FAB) 360 (MH$^+$)

Example 15

Production of (3S) -1-acetoxy-3-(N-benzyloxycarbonyl)amino-1-methylthio-2-oxo-4-phenylbutane:

404.5 mg (1.125 mmol) of (3S)-3-N-benzyloxycarbonylamino-1-hydroxy-1-methylthio-2-oxo-4-phenylbutane was dissolved in 11 ml of dichloromethane and 0.27 ml of pyridine, and 0.12 ml (1.69 mmol) of acetyl chloride was added thereto, while cooling it in an ice bath, and then stirred at room temperature for 3 hours and 30 minutes. The reaction mixture was extracted with 20 ml of 0.5N hydrochloric acid and 15 ml of dichloromethane. The resulting organic layer was washed with 12 ml of a saturated aqueous solution of sodium hydrogen carbonate and 15 ml of a saturated saline solution, and then dried with anhydrous sodium sulfate. This was filtered and concentrated, and the resulting residue was purified through silica gel column chromatography (hexane/ethyl acetate=from 5/1 to 4/1) to obtain 413.3 mg (1.029 mmol) of the above-entitled compound. The yield was 91.5%. The integral ratio in $^1$H-NMR of the compound verified that the compound is a mixture of diastereomers of about 1:1.

$^1$H-NMR (300 MHz, CDCl$_3$)

δ: 1.75 (s, 3/2H), 1.98 (s, 3/2H), 2.14 (s, 3/2H), 2.17 (s, 3/2H), 2.99 (m, 1H), 3.17 (m, 1H), 4.97–5.29 (m, 4H), 6.01 (s, 1/2H), 6.15 (s, 1/2H), 7.17–7.37 (m, 10H)

Mass spectrum (FA-B) 402 (MH$^+$)

Example 16

Production of methylthio (3S)-(2R,S)-2-acetoxy-3-(N-benzyloxycarbonyl)amino-4-phenylbutyrate:

124.5 mg (0.310 mmol) of (3S)-1-acetoxy-3-N-benzyloxycarbonylamino-1-methylthio-2-oxo-4-phenylbutane was dissolved in 3 ml of toluene, and 0.05 ml (0.334 mmol) of 1,8-diazabicyclo[5.4.0]undec-7-ene was added thereto. After having been stirred at room temperature for 1 hour and 55 minutes, this was extracted with 15 ml of ethyl acetate and 7 ml of 1N hydrochloric acid. The resulting organic layer was washed with 7 ml of a saturated aqueous solution of sodium hydrogen carbonate and 7 ml of a saturated saline solution, then dried with anhydrous sodium sulfate, filtered and concentrated. The resulting residue was purified through partitioning, silica gel thin-layer chromatography to obtain 121.4 mg (0.302 mmol) of the above-entitled compound. The yield was 97.5%. The integral ratio in $^1$H-NMR of the compound verified that the ratio of the diastereomers constituting it is about 6:4.

$^1$H-NMR (300 MHz, CDCl$_3$)

δ: 2.18 (s, 3H), 2.25 (s, 6/5H), 2.31 (s, 9/5H), 2.77–2.99 (m, 2H), 4.53 (m, 1H), 4.81 (br. d, 2/5H, —NH), 5.04 (d, 2H), 5.11 (br. d, 3/5H, —NH), 5.21 (d, 3/5H), 5.43 (d, 2/5H), 7.16–7.38 (m, 10H).

Mass spectrum (FAB) 402 (MH+)

Example 17

Production of (3S)-1-acetoxy-3-(N-benzyoxycarbonyl)amino-1-methylthio-2-oxo-phenylbutane (I, R$^1$=benzyloxycarbonyl, R$^2$=H, R$^3$=benzyl, R$^4$=acetyl, R$^5$=methyl)

166.2 mg (0.462 mmol) of (3S)-3-(N-benzyoxycarbonyl)amino-1-methylsulfinyl-2-oxo-phenylbutane was dissolved in 4.6 ml of dichloromethane, 0.5 ml of pyridine and 0.5 ml of acetic anhydride, and 3 mg of 4-dimethylaminopyridine was added thereto, and stirred at room temperature for 17.5 hours. To the reaction mixture was added 15 ml of ethyl acetate and 10 ml of 1N hydrochloric acid. The resulting organic layer was washed with 10 ml of a saturated aqueous solution of sodium hydrogencarbonate and 10 ml of a saturated saline solution, and then dried with anhydrous sodium sulfate. This was filtered and concentrated, and the resulting residue was purified through silica gel thin-layer chromatography to obtain 124.5 mg (0.310 mmol) of the above-entitled compound. The yield was 67.1%.

Example 18

Production of (3S)-1-acetoxy-3-(N,N-dibenzyl)amino-1-methylthio-2-oxo-phenylbutane (I, R$^1$=benzyloxycarbonyl, R$^2$=R$^3$=benzyl, R$^4$=acetyl, R$^5$=methyl)

102.4 mg (0.252 mmol) of (3S)-3-(N,N-dibenzy)amino-1-methylsulfinyl-2-oxo-phenylbutane was dissolved in 2 ml of dichloromethane, 0.2 ml of pyridine and 0.2 ml of acetic anhydride, and 3 mg of 4-dimethylamino-pyridine was added thereto, and stirred at room temperature for 10 days. To the reaction mixture was added 10 ml of ethyl acetate and 10 ml of 1N hydrochloric acid. The resulting organic layer was washed with 6 ml of water, 7 ml of a saturated aqueous solution of sodium hydrogencarbonate and 7 ml of a saturated saline solution, and then dried with anhydrous sodium sulfate. This was filtered and concentrated, and the resulting residue was purified through silica gel thin-layer chromatography to obtain 86.6 mg (0.193 mmol) of the above-entitled compound. The yield was 76.8%.

Example 19

Production of (3S)-3-(N,N-dibenzyl)amino-1-methylsulfinyl-2-oxo-4-phenylbutane (V, R$^1$=R$^2$=R$^3$=benzyl, R$^5$=methyl)

3.55 g (91.0 mmol) of sodium amide was suspended in 53 ml of tetrahydorofuran and 10.8 ml (152 mmol) of dimethylsulfoxide and heated at from 47° to 51° C. for 3 hours. The resulting suspension was cooled to −12° C. To this was dropwise added a solution of 13.63 g (96.9 wt %, 30.33 mmol) of N,N-dibenzyl-L-phenylalanine methyl ester as dissolved in 18 ml of tetrahydrofuran, while keeping it at −12° to −6° C. for 35 minutes. After these were reacted at −12° to −8° C. for 1 hour, 110 ml of an aqueous solution of 10% citric acid and 44 ml of ethyl acetate were added to the reaction mixture, which was thus subjected to phase separation. The organic layer was washed with 30 ml of a saturated aqueous solution of sodium hydrogencarbonate and 30 ml of a saturated saline solution. This was dried with anhydrous sodium sulfate, filtered and concentrated to obtain the crude above-entitled compound. As the result of HPLC analysis, 12.38 g (30.53 mmol) of the above-entitled compound was obtained. The yield was 100%.

Example 20

Production of (3S)-3-(N,N-dibenzyl)amino-1-hydroxy-1-methylthio-2-oxo-phenylbutane hydrogen chloride salt (VI, R$^1$=R$^2$=R$^3$=benzyl, R$^5$=methyl)

The crude compound of (3S)-3-(N,N-dibenzyl)amino-1-methylsulfinyl-2-oxo-4-phenylbutane (12.38 g (30.53 mmol)) obtained in Example 19 was dissolved in 68 ml of acetone and 22.8 ml of dimethylsulfoxide, and 22.8 ml of 2N hydrochloric acid was added thereto and stirred at 30° C. for 16 hours. While being cooled in an ice bath, this was neutralized with 50 ml of a saturated aqueous solution of sodium hydrogencarbonate, and concentrated to remove acetone. Then the resulting solution was subjected to phase separation with 60 ml of ethyl acetate. The organic layer was washed with 40 ml of a saturated saline solution, and thereafter dried with anhydroussodium sulfate. This was filtered and concentrated, and the resulting residue was dissolved in 45.5 ml of ethyl acetate and 55 ml of hexane. To this was dropwise added 9.1 ml of 4N hydrogen chloride solution in ethyl acetate. The resulting solid was filtered and washed with 45 ml of ethyl acetate/hexane=1/2, and dried to obtain 11.48 g of a crude product of the above-entitled compound.

Example 21

Production of (3S)-1-acetoxy-3-(N,N-dibenzyl)amino-1-methylthio-2-oxo-phenylbutane (I, $R^1=R^2=R^3$=benzyl, $R^4$=acetyl, $R^5$=methyl)

11.48 g of the crude product of (3S)-3-(N,N-dibenzyl) amino-1-hydroxy-1-methylthio-2-oxo-phenylbutane hydrogen chloride salt as obtained in Example 20 was dissolved in 52 ml of dichloromethane and 4.62 ml of pyridine, and 2.22 ml of acetyl chloride was added thereto, while cooling in an ice bath for 5 minutes, and stirred at 10° C. for 1 hour. The reaction mixture was extracted with 30 ml of an aqueous solution of 10% citric acid. The resulting organic layer was washed with 30 ml of a saturated aqueous solution of sodium hydrogencarbonate and 30 ml of a saturated saline solution, and then dried with anhydrous sodium sulfate. This was filtered and concentrated to obtain the crude above-entitled compound. As the result of HPLC analysis, this crude product contained 9.395 g (20.99 mmol) of the above-entitled compound, and the yield was 69.2% (2 steps).

Example 22

Production of methylthio (2S,3S)-2-acetoxy-3-(N,N-dibenzy 1)amino-4-phenylbutyrate (II, $R^1=R^2=R^3$=benzyl, $R^4$=acetyl, $R^5$=methyl)

The crude compound of (3S)-1-acetoxy-3-(N,N-dibenzyl) amino-1-methylthio-2-oxo-phenylbutane (9.39S g (20.99 mmol)) as obtained in Example 21 was dissolved in 45 ml of N,N-dimethylformamide and cooled to −31° C., and a solution of 641 mg (4.21 mmol) of 1,8-diazabicyclo[5,4,0] undec-7-ene as dissolved in 3 ml of N,N-dimethylformamide was added thereto for 10 minutes. After having been stirred at −30° C. for 16 hours, this was extracted with 50 ml of an aqueous solution of 10% citric acid and 77 ml of ethyl acetate. The resulting organic layer was washed with 50 ml of water+10 ml of a saturated saline solution, 30 ml of a saturated aqueous solution of sodium hydrogencarbonate, and 30 ml of a saturated saline solution in that order, and then dried with anhydrous sodium sulfate. This was filtered and concentrated to the crude above-entitled compound. As the result of HPLC analysis, the ratio of diastereomers constituting it, of (2S,3S):(2R,3S), is about 89:11 and 8.101 g (18.10 mmol) of (2S,3S)-diastereomer was obtained. The yield of (2S,3S)-diastereomer was 86.2%.

Example 23

Production of (2S,3S)-3-(N,N-dibenzyl)amino-2-hydroxy-4-phenylbutyric acid dicyclohexylamine salt (VII,$R^1=R^2=R^3$=benzyl, $R^7$=H)

The crude compound of methylthio (2S,3S)-2-acetoxy-3-(N,N-dibenzyl)amino-4-phenylbutyrate (8.101 g (18.10 mmol)) as obtained in Example 22 was dissolved in 90 ml of methanol, and 36 ml of 2N aqueous solution of sodium hydroxide was added thereto and stirred at room temperature for 3.5 hours. After these were concentrated to remove methanol, 50 ml of dichloromethane and 12 ml of 6N hydrochloric acid to adjust to pH 1.9 were added to the reaction mixture. After separation, the resulting organic layer was washed with 30 ml of saturated saline solution, and then dried with anhydrous sodium sulfate. This was filtered and concentrated, and the resulting residue was dissolved in 50 ml of acetone. After filtration to remove the insoluble matter and washing it with 30 ml of acetone, to this filtrate was dropwise added 4.43 g (24.43 mmol) of dicyclohexylamine and the resulting crystal was filtered and washed with 30 ml of acetone, and dried under vacuum to obtain 9.02 g (95.0 wt %, 15.39 mmol) of the above-entitled compound. The yield was 85.0%.

$^1$H-NMR (300 MHz, CDCl$_3$)

δ: 0.95–1.42 (m, 5H), 1.50–1.97 (m, 5H), 2.48 (dd, 1H), 2.77 (m, 2H), 3.03 (dd, 1H), 3.50 (ddd, 1H), 3.60 (d, 2H), 4.02 (d, 2H), 4.44 (d, 1H), 6.95–7.35 (m, 15H)

$^{13}$C-NMR (75 MHz, CDCl$_3$)

δ: 24.61, 25.07, 28.96, 32.69, 52.29, 54.09, 62.06, 69.93, 125.50, 126.21, 127.68, 127.77, 128.55, 129.73, 140.63, 140.83, 178.18.

Mass spectrum (FAB) 557 (MH$^+$)

Example 24

Production of (3S)-3-(N,N-dibenzyl)amino-1-methylsulfinyl-5-methyl-2-oxo-hexane (V, $R^1=R^2$=benzyl, $R^3$=isobutyl, $R^5$=methyl)

1.00 g (25.63 mmol) of sodium amide was suspended in 10 ml of dimethylsulfoxide and heated at from 50° to 60° C. for 30 minutes. 10 ml of tetrahydrofuran was added to the resulting solution and cooled to −5° C. To this was dropwise added a solution of 3.38 g (10.39 mmol) of N,N-dibenzyl-(L)-leucine methyl ester as dissolved in 6.5 ml of tetrahydrofuran, while keeping it at −5° C. for 40 minutes. After these were reacted at −5° C. for 1 hour and 20 minutes, 40 ml of an aqueous solution of 10% citric acid and 50 ml of ethyl acetate were added to the reaction mixture which was thus subjected to phase separation. The organic layer was washed with 30 ml of a saturated aqueous solution of sodium hydrogencarbonate and 20 ml of a saturated saline solution. This was dried with anhydrous sodium sulfate, filtered and concentrated, and the resulting residue was purified through silica gel column chromatography (hexane/ethyl acetate=1/1 to 1/3) to obtain 3.86 g of the above-entitled compound. The yield was 100%. The integral ratio in $^1$H-NMR of the compound verified that the ratio of the diastereomers constituting it is about 1:1.

$^1$H-NMR (300 MHz, CDCl$_3$)

δ: 0.80 (d, 3/2H), 0.86 (d, 3/2H), 0.89 (d, 3/2H), 0.90 (d, 3/2H), 1.36–1.50 (m, 2H), 1.83 (m, 1H), 2.57 (s, 3/2H), 2.61 (s, 3/2H), 3.34 (br. d, 1H), 3.48 (dd, 2H), 3.72 (br. d, 2H), 3.81–3.96 (m, 3/2H), 4.09 (d, 1/2H), 7.24–7.39 (m, 10H).

Mass spectrum (ESI) 372 (MH$^+$)

Example 25

Production of (3S) -3-(N,N-dibenzyl)amino-1-hydroxy-1-methylthio-5-methyl-2 -oxo-hexane (VI, $R^1=R^2$=benzyl, $R^3$=isobutyl, $R^5$=methyl)

2.35 g (6.324 mmol) of (3S)-3-(N,N-dibenzyl)amino-1-methylsulfinyl-5-methyl-2-oxo-hexane was dissolved in 19 ml of dimethylsulfoxide, and 4.74 ml of 2N hydrochloric acid was added thereto and stirred at 30° C. for 14 hours. While being cooled in an ice bath, this was neutralized with 15 ml of a saturated aqueous solution of sodium hydrogencarbonate, and then subjected to phase separation with 30 ml of ethyl acetate and 20 ml of water. The organic layer was washed with 20 ml of water and 20 ml of a saturated saline solution in that order, and thereafter dried with anhydrous sodium sulfate.

This was filtered and concentrated to obtain 2.16 g of a crude product of the above-entitled compound. The integral ratio in $^1$H-NMR of the compound verified that the compound is a mixture of diastereomers of about 10:1. The data of the major diastereomerase shown below.

$^1$H-NMR (300 MHz, CDCl$_3$)

δ: 0.85 (d, 3/2H), 0.94 (d, 3/2H), 1.35–1.50 (m, 2H), 1.74 (s, 3H), 1.93 (m, 1H), 3.41 (d, 2H), 3.68 (d, 2H), 3.82–3.90 (m, 2H), 5.50 (br. s, 1H), 7.23–7.36 (m, 10H).

Example 26

Production of (3S)-1-acetoxy-3-(N,N-dibenzyl)amino-1-methylthio--5-methyl-2-oxo-hexane (I, $R^1=R^2$=benzyl, $R^3$=isobutyl, $R^4$=acetyl, $R^5$=methyl)

1.66 g (4.47 mmol) of the crude product of (3S)-3-(N,N-dibenzyl)amino-1-hydroxy-1-methylthio-5-methyl-2-oxo-hexane as obtained in Example 25 was dissolved in 16 ml of dichloromethane and 0.54 ml of pyridine, and 0.38 ml of acetyl chloride was added thereto, while cooling in an ice bath, and stirred at room temperature for 1 hour. The reaction mixture was extracted with 15 ml of an aqueous solution of 10% citric acid and 10 ml of dichloromethane as added thereto. The resulting organic layer was washed with 15 ml of a saturated aqueous solution of sodium hydrogen-carbonate and 15 ml of a saturated saline solution, and then dried with anhydrous sodium sulfate. This was filtered and concentrated, and the resulting residue was purified through partitioning, silica gel column chromatography to obtain 1.48 g (3.58 mmol) of above-entitled compound. The yield was 80.1%. The integral ratio in $^1$H-NMR of the compound verified that the compound is a mixture of diastereomers of about 10:1. The data of the major diastereomer are shown below.

$^1$H-NMR (300 MHz, CDCl$_3$)

δ: 0.83 (d, 3H), 0.91 (d, 3H), 1.38–1.47 (m, 2H), 1.84 (s, 3H), 1.86 (m, 1H), 2.18 (s,3H), 3.43 (d,2H), 3.72 (d, 2H), 3.84 (dd, 1H), 6.48 (s, 1H), 7.22–7.37 (m,10H).

Mass spectrum (ESI) 414 (MH$^+$)

Example 27

Production of methylthio (2S,3S)-2-acetoxy-3-(N,N-dibenzyl)amino-5-methylhexanoate (II, $R^1=R^2$=benzyl, $R^3$=isobutyl, $R^4$=acetyl, $R^5$=methyl)

0.61 g (1.48 mmol) of (3S)-1-acetoxy-3-(N,N-dibenzyl)amino-1-methylthio-5-methyl-2-oxo-hexane was dissolved in 7.5 ml of N,N-dimethylformamide and cooled to −30° C., and 0.066 ml of 1,8-diazabicycl[5,4,0]undec-7-ene was added thereto. After having been stirred at −30° C. for 15.5 hours, this was extracted with 20 ml of an aqueous solution of 10% citric acid and 30 ml of ethyl acetate. The resulting organic layer was washed with 20 ml of a saturated aqueous solution of sodium hydrogen-carbonate and 20 ml of a saturated saline solution, and then dried with anhydrous sodium sulfate. This was filtered and concentrated, and the resulting residue was purified through partitioning, silica gel column chromatography to obtain 0.60 g of above-entitled compound. The yield was 98%. The integral ratio in $^1$H-NMR of the compound verified that the ratio of diastereomers constituting it of (2S,3S):(2R,3S), is about 95:5. The data of the major diastereomer ((2S,3S)-form) are shown below.

$^1$H-NMR (300 MHz, CDCl$_3$)

δ: 0.37 (d, 3H), 0.87 (d, 3H), 1.01 (m, 1H), 1.76–1.86 (m, 2H), 2.23 (s, 3H), 2.26 (s, 3H), 3.25 (m, 1H), 3.31 (d, 2H), 3.592 (d, 2H), 5.83 (d, 1H), 7.21–7.33 (m, 10H)

Mass spectrum (ESI) 414 (MH$^+$)

Having now fully described the invention, it will be apparent to one of ordinary skill in the art that many changes and modifications can be made thereto without departing from the spirit or scope of the invention as set forth herein.

This application is based on JP 257497/1995 filed in Japan on Oct. 4, 1995. The full text of the priority document is incorporated herein by reference.

What is claimed as new and desired to be secured by Letters Patent of the United States is:

1. A method for producing α-acyloxy-thioesters of the formula (II):

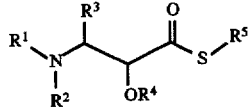

wherein $R^1$ represents an unsubstituted or substituted, linear, branched or cyclic alkanoyl group having from 2 to 18 carbon atoms, an unsubstituted or substituted, linear, branched or cyclic alkoxycarbonyl group having from 2 to 18 carbon atoms, an aralkyloxy carbonyl group having from 7 to 18 carbon atoms, or an unsubstituted or substituted benzyl group, or represents, together with $R^2$, a residue of a dibasic acid having from 8 to 18 carbon atoms;

$R^2$ represents a hydrogen atom or an unsubstituted or substituted benzyl group, or represents, together with $R^1$, a residue of a dibasic acid having from 8 to 18 carbon atoms;

$R^3$ represents an unsubstituted or substituted, linear, branched or cyclic alkyl group having from 1 to 18 carbon atoms, an aralkyl group having from 7 to 18 carbon atoms, or an aryl group having from 6 to 18 carbon atoms;

$R^4$ represents an unsubstituted or substituted, linear, branched or cyclic alkanoyl group having from 2 to 18 carbon atoms, or an arylcarbonyl group having from 7 to 18 carbon atoms; and $R^5$ represents an alkyl group having 1 or 2 carbon atoms, an aryl group having from 6 to 18 carbon atoms, or an aralkyl group having from 7 to 18 carbon atoms, which comprises rearranging, in the presence of a base, an α-keto-hemimercaptal-carboxylate of the formula (I):

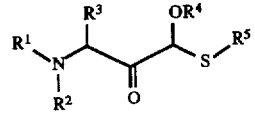

wherein $R^1$, $R^2$, $R^3$, $R^4$ and $R^5$ have the same meanings as above.

2. The method of claim 1, in which the compound of formula (I) is obtained by reacting an N-protected α-aminocarboxylate of the formula (III):

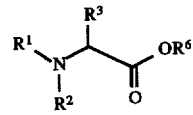

wherein $R^1$ represents an unsubstituted or substituted, linear, branched or cyclic alkanoyl group having from 2 to 18 carbon atoms, an un substituted or substituted, linear, branched or cyclic alkoxycarbonyl group having from 2 to 18 carbon atoms, an aralkyloxycarbonyl group having from 7 to 18 carbon atoms, or an unsubstituted or substituted benzyl group, or represents, together with $R^2$, a residue of a dibasic acid having from 8 to 18 carbon atoms;

$R^2$ represents a hydrogen atom or an unsubstituted or substituted benzyl group, or represents, together with $R^1$, a residue of a dibasic acid having from 8 to 18 carbon atoms;

$R^3$ represents an unsubstituted or substituted, linear, branched or cyclic alkyl group having from 1 to 18 carbon atoms, an aralkyl group having from 7 to 18 carbon atoms, or an aryl group having from 6 to 18 carbon atoms; and $R^6$ represents a linear or branched alkyl group having from 1 to 5 carbon atoms, an aryl group having from 6 to 18 carbon atoms; or an aralkyl group having from 7 to 18 carbon atoms, with a carbanion of the formula (IV):

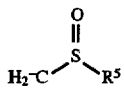

wherein $R^5$ represents an alkyl group having 1 or 2 carbon atoms, an aryl group having from 6 to 18 carbon atoms, or an aralkyl group having from 7 to 18 carbon atoms, to a β-ketosulfoxide of the formula (V):

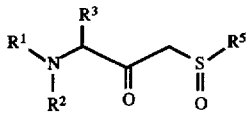

wherein $R^1$, $R^2$, $R^3$ and R5' have the same meanings as above, then reacting the sulfoxide with an acid to obtain an hemimercaptal of the formula (VI):

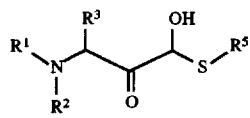

wherein $R^1$, $R^2$, $R^3$ and $R^5$ have the same meanings as above, and thereafter acylating the hemimercaptal.

3. The method of claim 1, in which $R^3$ in formula (I) is bonded to the carbon atom as existing therein in the S-configuration.

4. The method of claim 1, in which $R^3$ in formula (I) is bonded to the carbon atom as existing therein in the R-configuration.

* * * * *